(12) United States Patent
Gilmour

(10) Patent No.: US 7,601,131 B2
(45) Date of Patent: Oct. 13, 2009

(54) CHAFE AND/OR A WALKER

(75) Inventor: Robert Farrer Gilmour, Auckland (NZ)

(73) Assignee: VQ Orthocare, Irvine, CA (US)

( * ) Notice: Subject to any disclaimer, the term of this patent is extended or adjusted under 35 U.S.C. 154(b) by 95 days.

(21) Appl. No.: 10/506,474

(22) PCT Filed: Mar. 5, 2003

(86) PCT No.: PCT/NZ03/00041

§ 371 (c)(1),
(2), (4) Date: Aug. 19, 2005

(87) PCT Pub. No.: WO03/073966

PCT Pub. Date: Sep. 12, 2003

(65) Prior Publication Data

US 2005/0283101 A1    Dec. 22, 2005

(30) Foreign Application Priority Data

Mar. 5, 2002    (NZ) .................................. 517593

(51) Int. Cl.
*A61F 5/00* (2006.01)
*A61F 13/00* (2006.01)
*A61F 5/37* (2006.01)
*A61F 13/06* (2006.01)

(52) U.S. Cl. .............. 602/27; 602/5; 602/23; 602/65; 128/882; 128/892; 24/700; 24/701; 24/697.1

(58) Field of Classification Search ............ 602/27, 602/5, 23, 65; 70/170–173, DIG. 57; 24/700–701, 24/697.1, DIG. 43–DIG. 44; 292/8, 42, 106, 292/265

See application file for complete search history.

(56) References Cited

U.S. PATENT DOCUMENTS

| | | | | |
|---|---|---|---|---|
| 1,947,773 A * | 2/1934 | Haviland | .................. | 292/292 |
| 4,993,127 A * | 2/1991 | Mechem et al. | .............. | 24/701 |
| 5,220,816 A * | 6/1993 | Fish et al. | .................... | 70/214 |
| 5,311,972 A * | 5/1994 | Plath | ......................... | 190/102 |
| 5,716,336 A * | 2/1998 | Hines et al. | .................. | 602/27 |
| 5,836,626 A * | 11/1998 | Coy | ........................... | 292/292 |
| 5,954,075 A | 9/1999 | Gilmour | | |
| 6,155,998 A | 12/2000 | Gilmour | | |
| 6,361,515 B1 | 3/2002 | Gilmour | | |
| 6,394,117 B1 * | 5/2002 | Gilmour | ...................... | 135/84 |
| D473,654 S * | 4/2003 | Iglesias et al. | ............. | D24/192 |
| 6,872,053 B2 * | 3/2005 | Bucher et al. | ........... | 416/210 R |

* cited by examiner

*Primary Examiner*—Patricia M Bianco
*Assistant Examiner*—Brandon Jackson
(74) *Attorney, Agent, or Firm*—Sheppard Mullin Richte & Hampton; David E. Heisey

(57) ABSTRACT

The present invention is directed to a chafe useable on an orthopedic walker and including members which define a slot through which a strap, such as the strap of a walker, may pass. The chafe also includes a stud on the member, and a connection element connecting the stud and members defining the slot.

8 Claims, 3 Drawing Sheets

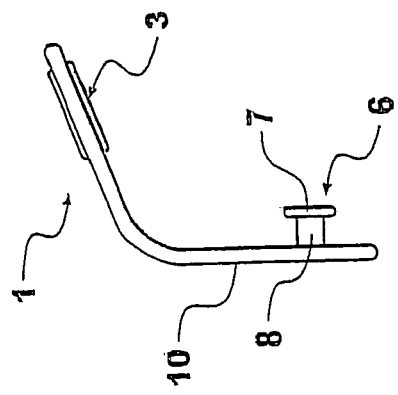
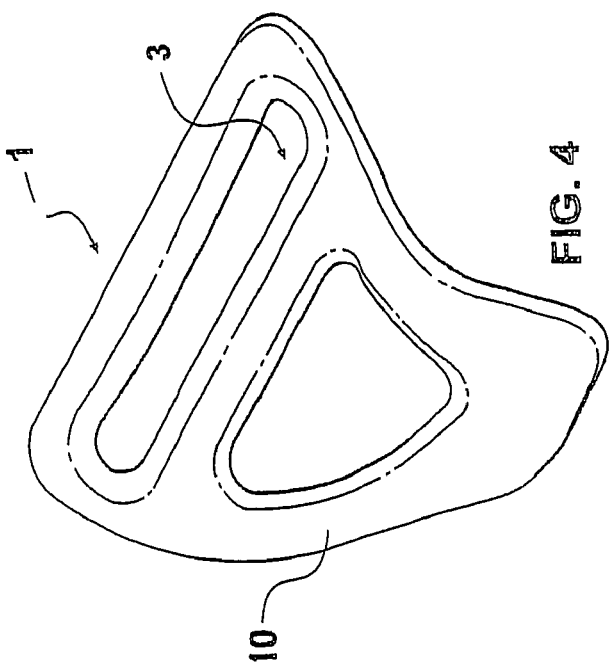
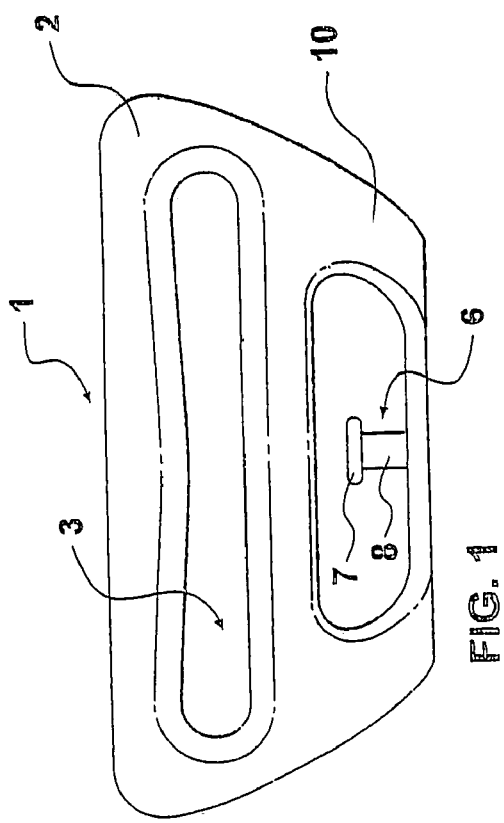
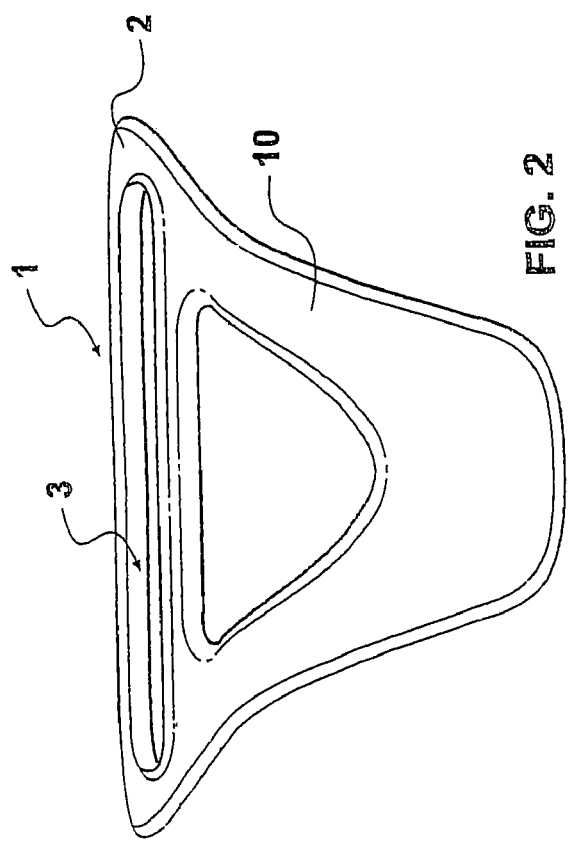

CHAFE AND/OR A WALKER

TECHNICAL FIELD

This invention relates to a chafe and/or a walker and has been designed particularly, though not necessarily solely, for use in connection with orthopaedic walkers.

BACKGROUND ART

Walkers are devices that are used for the immobilisation and protection of the lower leg, ankle and foot of a user. The walker has uprights which are attached to either side of the leg, and these uprights can either be fixed at 90° to the ground or there can be a provision for the uprights to be fixed in a range of positions, or pass through a range of permissible ankle movement.

It is common for walkers to come in a limited range of sizes (usually three or four), and these are required to fit a substantial range of foot sizes. Furthermore the foot could be bandaged. The foot is commonly held in place by two straps passing over the foot once it is placed into the main body of the walker.

Commonly the straps either pass through slots in the side of the walker body, or through chafes which are attached to the main body of the walker by screws or rivets. Commonly these slots or chafes determine the position of the straps. Chafes have the advantage of providing more adaptability to foot contour and they make fitting of both the walker and also the straps easier.

The straps across the dorsum of the foot ideally exert even pressure on the foot so as not to inhibit circulation and so as to provide maximum stability and comfort at a minimum pressure. However the position of the straps is not always ideal particularly where they are needed to be fitted over a bandaged foot following surgery or injury.

In these instances the contour of the dorsum of the foot may not resemble a presumed average foot shape and so strap fixation is compromised.

This is clearly disadvantageous.

OBJECT OF THE INVENTION

It is therefore an object of the present invention to provide a chafe and/or a walker and chafe which will obviate or minimise the foregoing disadvantages in a simply yet effective manner or which will at least provide the public with a useful choice.

STATEMENT OF THE INVENTION

Accordingly in one aspect the invention consists in a chafe comprising a member having a slot therein, a stud, and connection means connecting the stud and member having the slot therein.

Preferably the member having the slot therein and the connection means are formed as a unitary construction.

Preferably the member having the slot therein, the connection means and the stud are formed as a unitary construction.

Preferably the stud has an enlarged head.

In a further aspect the invention consists in a walker frame having at least one set of apertures, the or each set of apertures having at least two apertures therein, and at least one chafe according to any one of the preceding paragraphs, each aperture being shaped so that the stud can be passed therethrough and optionally held in the aperture or released therefrom.

Preferably at least two sets of apertures are provided.

Preferably each aperture has a narrower upper end in use, and a wider lower part in use, so that the head of a stud can pass through the lower part of the aperture but be retained by the material defining the upper part of the aperture.

Preferably at least one set of apertures has an associated slot in the walker frame.

Preferably each set of apertures has an associated slot in the walker frame.

Preferably the upper edge of the slot is formed to a saw tooth pattern, the edges of each upwardly extending part, in use, being such that the head of the stud will be retained therein.

To those skilled in the art to which the invention relates, many changes in construction and widely differing embodiments and applications of the invention will suggest themselves without departing from the scope of the invention as defined in the appended claims. The disclosures and the description herein are purely illustrative and are not intended to be in any sense limiting.

BRIEF DESCRIPTION OF THE DRAWINGS

One preferred form of the invention will now be described with reference to the accompanying drawings in which, FIG. 1 is a plan view of a chafe according to one preferred form of the invention, FIG. 2 is a side elevation of a chafe according to one preferred form of the invention, FIG. 3 is an end elevation of a chafe according to one preferred form of the invention, FIG. 4 is a perspective view of a chafe according to one preferred form of the invention.

BEST MODE FOR CARRYING OUT THE INVENTION

Figure 7:
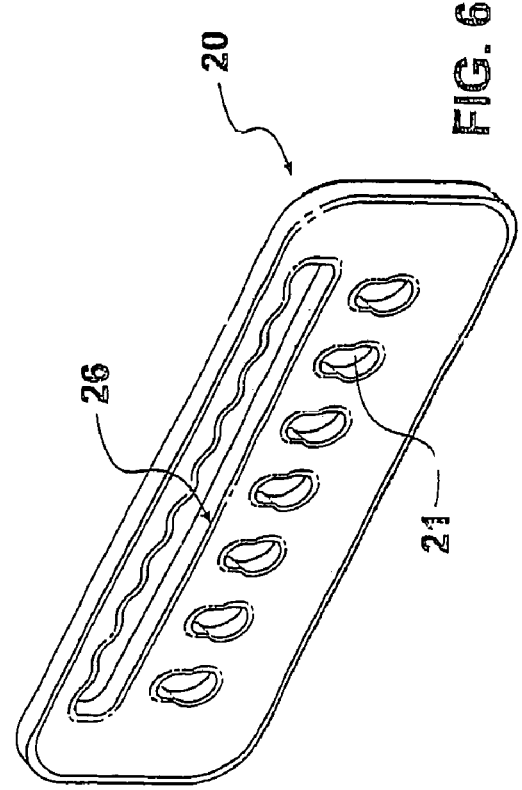
FIG. 7 is a perspective view of the construction of FIG. 5 in engagement with a chafe as shown in any one of FIGS. 1 to 4.

In the preferred form of the invention a chafe 1 is provided. The chafe 1 comprises members 2 which define a slot 3 through which a strap, such as the strap of a walker for fixing the walker to a foot, may pass. The chafe 1 also includes a stud 6 which preferably has an enlarged head 7 mounted on a stem 8. The members 2 and the stud 6 are interconnected by connection means 10 in the form of a member or bifurcated member, as shown in FIGS. 1 to 4, extending from the members 2. In the preferred form the members 2 and the connecting means 10 are formed as a unitary member and further in the preferred form the stud 6 also forms part of the same unitary member.

The chafe 1 can therefore be moulded from a suitably strong yet resilient plastics material.

Also provided as part of the walker frame 12 or as a separate member attachable to the walker frame is a member 20 which provides a set of apertures having at least two apertures 21 and in the embodiments shown there are seven such apertures.

Figure 8:
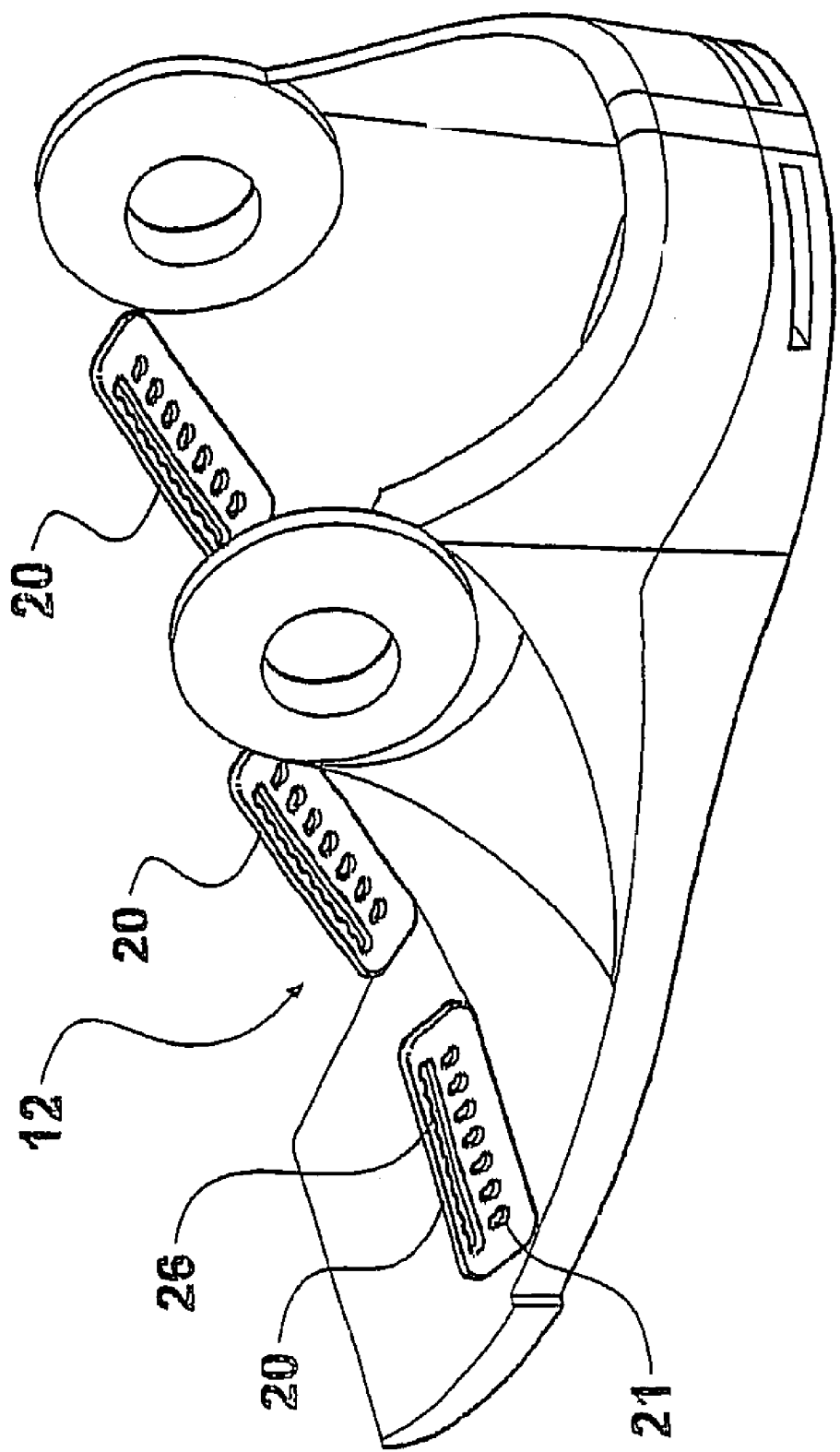
FIG. 8 is a perspective diagrammatic view of a walker according to one preferred form of the invention.

A set of apertures 21 is provided at each point where it is desired to affix or change the direction of a fixing strap on the walker. Accordingly there may be, for example, two or four such positions on the walker frame, there being one or two such positions towards each side of the foot when the walker frame is in use. Four such positions are indicated in FIG. 8 (one being hidden).

Each aperture 21 is provided so that it has an upper part 22 and a lower part 23 when the construction is in use.

The construction is such that the head 7 of a stud 6 may pass through the lower part 23 of the aperture but be retained in position by engagement with the material surrounding the upper part 22. Other methods of optionally holding or releasing the stud may be used such as for example, providing the head 7 in an oblong shape so that in one orientation the head can pass through the aperture, but in the other orientation at substantially 90° be retained or otherwise as desired.

Figure 5:
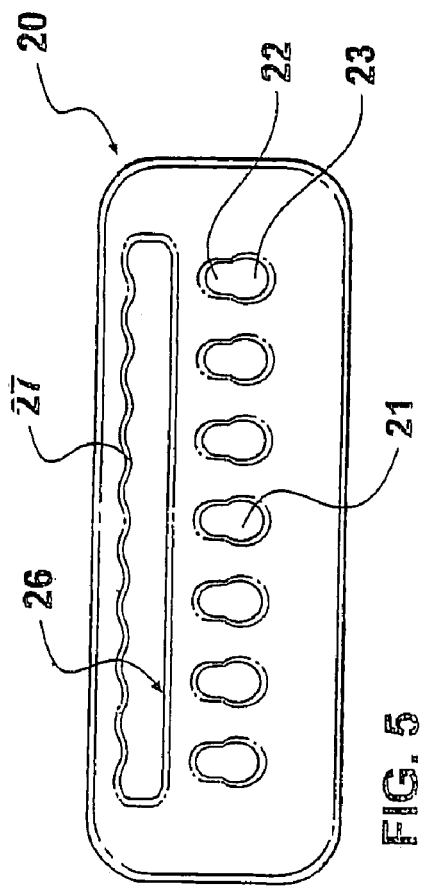
FIG. 5 is a front elevation of part of a walker frame or a member attachable to a walker frame according to one preferred form of the invention.
Figure 6:
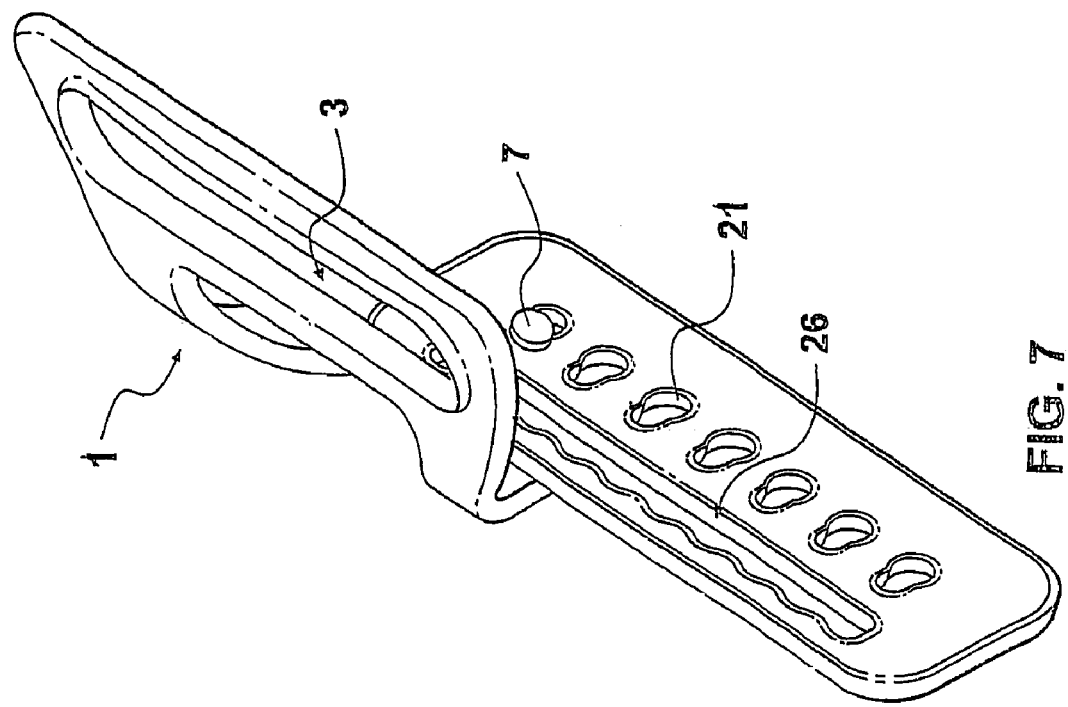
FIG. 6 is a perspective view of the construction of FIG. 5.

In the preferred form, also associated with the apertures 21, is provided a slot 26. The slot 26 preferably has the upper edge, in use, 27 thereof, formed to a saw tooth shape as can be seen in FIG. 5. Preferably the dimensions of the saw teeth 27 are such that the stem 8 of the stud 6 can be retained in the saw teeth, in particular by means of engagement of the head 7 with the material defining the saw tooth pattern.

In use a chafe 1 may be connected with the walker frame element 20 by passing the head 7 and a stud 6 through an aperture 21 at the part 23 and moving the head into engagement in the part 22. The chafe will be free to rotate for fixing but is also readily removed by moving the head 7 adjacent the lower part 23 and again withdrawing it from the member 20. The chafe can then be repositioned.

As an alternative the chafe can be positioned in the saw tooth slot 26 or alternatively straps themselves can be passed through the saw tooth slot 26 where the teeth will effect a gripping motion on the strap helping to maintain the strap in the position that it has been originally located.

Thus it can be seen that at least in the preferred form of the invention a chafe and/or a walker are provided which has the advantage that substantial flexibility as to the position and angle of the chafe in relation to the walker frame is available. This allows the best position of a strap in relation to the dorsum of the foot to be achieved thereby enhancing comfort and stability whilst minimising any tendency for the straps to inhibit circulation.

I claim:

1. A walker, comprising:
    a frame having at least one set of substantially collinear apertures and a slot, wherein the collinear apertures and the slot are substantially coplanar, and
    at least one chafe comprising a member having a slot therein, a stud, and connection means connecting the stud and member having the slot therein,
    wherein the member having the connection means and the stud are formed as a unitary construction independent of the frame, and
    wherein each aperture is shaped so that the stud can be passed head first therethrough, held in the aperture and released therefrom.

2. The walker of claim 1 wherein the stud has an enlarged head.

3. The walker of claim 1 wherein at least two sets of apertures are provided.

4. The walker of claim 3 wherein each aperture has a narrower upper end in use, and a wider lower part in use, so that the head of a stud can pass through the lower part of the aperture but be retained by the material defining the upper part of the aperture.

5. The walker of claim 4 wherein at least one set of apertures has an associated slot in the walker frame.

6. The walker of claim 4 wherein each set of apertures has an associated slot in the walker frame.

7. The walker of claim 5 wherein the upper edge of the slot is formed to a triangular saw tooth pattern, the edges of each upwardly extending part, in use, being such that the head of the stud will be retained therein.

8. The walker of claim 6 wherein the upper edge of the slot is formed. to a triangular saw tooth pattern, the edges of each upwardly extending part, in use, being such that the head of the stud will be retained therein.

* * * * *